US008540815B2

(12) United States Patent
Gbureck

(10) Patent No.: US 8,540,815 B2
(45) Date of Patent: Sep. 24, 2013

(54) PREPARATION FOR MAGNESIUM AMMONIUM PHOSPHATE CEMENTS

(75) Inventor: Uwe Gbureck, Wurzburg (DE)

(73) Assignee: InnoTERE GmbH, Dresden (DE)

( * ) Notice: Subject to any disclaimer, the term of this patent is extended or adjusted under 35 U.S.C. 154(b) by 310 days.

(21) Appl. No.: 12/918,591

(22) PCT Filed: Feb. 18, 2009

(86) PCT No.: PCT/DE2009/000218
§ 371 (c)(1),
(2), (4) Date: Oct. 11, 2010

(87) PCT Pub. No.: WO2009/103273
PCT Pub. Date: Aug. 27, 2009

(65) Prior Publication Data
US 2011/0028568 A1     Feb. 3, 2011

(30) Foreign Application Priority Data
Feb. 20, 2008 (DE) .................. 10 2008 010 210

(51) Int. Cl.
*C04B 12/02* (2006.01)
(52) U.S. Cl.
USPC .......................................... 106/690; 423/305
(58) Field of Classification Search
USPC ........................................ 106/690; 423/305
See application file for complete search history.

(56) References Cited

U.S. PATENT DOCUMENTS

| 4,518,430 | A | 5/1985 | Brown et al. |
| 5,605,713 | A | 2/1997 | Boltong |
| 6,692,563 | B2 * | 2/2004 | Zimmermann ............... 106/696 |
| 2005/0287071 | A1 | 12/2005 | Wenz |
| 2008/0020980 | A1 | 1/2008 | Zimmermann |

FOREIGN PATENT DOCUMENTS

| DE | 100 32 220 | 1/2002 |
| EP | 1 296 909 | 4/2003 |
| EP | 1 707 543 | 10/2006 |

OTHER PUBLICATIONS

Hench L.L., Wilson, J., "An Introduction to Bioceramics," Advanced Series in Ceramics—vol. I, World Scientific, 1993, vii-11.
Yamamuro, T., Hench L.L., Wilson, J., "Calcium Phosphate and Hydroxylapatite Ceramics," vol. II, Handbook of Bioactive Ceramics, CRC Press, 1990.
Aaboe, M., Pinholt, M., Hjorting-Hansen, E., "Healing of Experimentally Created Defects: A Review," British Journal of Oral & Maxillofacial Surgery, 1995, 33: 312-318.
Schmitz, J.P., Hollinger, J.O., Milam, S.B., "Reconstruction of Bone using Calcium Phosphate Bone Cements: A Critical Review," Journal of Oral & Maxillofacial Surgery, 1999, 57: 1122-1126.
Hench, L L., "Ceramics, Glasses, and Composites in Medicine," Association for the Advancement of Medical Instrumentation, 1973, vol. 7, No. 2, 136-144.
Zitzmann, N. U., Rateitschak-Pluss, E., Marinello, C.P., "Treatment of Angular Bone Defects with a Composite Bone Grafting Material in Combination with a Collagen Membrane," J Periodontol, May 2003, vol. 74, No. 5, 687-694.
Ramshaw, J.A.M., Werkmeister, J.A., Peters, D.E., "Collagen as a Biomaterial," Current Perspectives on Implantable Devices, 1990, vol. 2, 151-220.
Frayssinet, P., Rouquet, N., Tourenne, F., Fages, J., Hardy, D., Bonel, G., Cell-Degradation of Calcium Phosphate Ceramics, Cells and Materials, 1993, vol. 3, No. 4, 383-394.
Gross, K.A., Berndt, C.C., "Biomedical Application of Apatites," Reviews in Mineralogy & Geochemistry, 2002, vol. 48, 631-672.
Dorozhkin, S.V., Epple, M., "Biological and Medical Significance of Calcium Phosphates," Agnew. Chem. Int. Ed., 2002, vol. 41, 3130-3146.
Bohner, M., "Calcium Orthophosphates in Medicine: From Ceramics to Calcium Phosphate Cements," Injury, Int. J. Care Injured, 2000, vol. 31, S-D37-47.
Breusch, S.J., Kuhn, K.D., "Knochenzemente auf Basis von Polymethylmethacrylat," Orthopade, 2003, vol. 32, 41-50.
Bohner, M., "Physical and Chemical Aspects of Calcium Phosphates used in Spinal Surgery," Eur Spine J, 2001, vol. 10, S114-S121.
Pittet, C., Lemaitre, J., "Mechanical Characterization of Brushite Cements: A Mohr Circles' Approach," Journal of Biomedical Materials Research, 2000, vol. 53, Issue 6, 769-780.
Theis, F., Apelt, D., Brand, B., Kutter, A., Zlinszky, K., Bohner, M., Matter, S., Frei, C., Auer, J.A., Von Rechenberg, B., "Biocompatibility and Resorption of a Brushite Calcium Phosphate Cement," Biomaterials, 2005, vol. 26, 4383-4394.
Oberle, A., Theiss, F., Bohner, M., Muller, J., Kastner, S.B., Frei, C., Boecken, I., Zlinszky, K., Wunderlin, S., Auer, J.A., Von Rechenberg, B., Untersuchungen uber den Klinischen Einsatz von Brushite-und Hydroxylpatit-Zement beim Schaf, (Investigation about the clinical use of brushite- and hydroxylapatite-cement in sheep), Schweizer Archiv fuer Tierhielkunde, 2005, vol. 147(11), 482-490.
Kuemmerle, J.M., Oberle, A., Oechslin, C., Bohner, M., Frei, C., Boecken, I., Von Rechenberg, B., "Assessment of the Suitability of a New Brushite Calcium Phosphate Cement for Cranioplasty—an Experimental Study in Sheep," Journal of Cranio-Maxillofacial Surgery, 2005, vol. 33, 37-44.
Bohner, M., "pH Variations of a Solution after Injecting Brushite Cements," Key Engineering Materials, 2001, vols. 192-195, 813-816.
Coe, F.L., Evan, A., Worcester, E., "Kidney Stone Disease," The Journal of Clinical Investigation, Oct. 2005, vol. 115, No. 10, 2598-2608.
Driessens, F.C.M., Boltong, M.G., Wenz, R., Meyer, J., "Calcium Phosphates as Fillers in Struvite Cements," Key Engineering Materials, 2005, vols. 284-286, 161-164.

(Continued)

*Primary Examiner* — Paul Marcantoni
(74) *Attorney, Agent, or Firm* — Emerson Thomson Bennett LLC; Roger D. Emerson; Daniel A. Thomson

(57) ABSTRACT

The invention relates to a preparation for a magnesium ammonium phosphate cement. There is provided a preparation comprising (a) a magnesium calcium phosphate of the formula $Mg_xCa_y(PO_4)_2O_z$, wherein $x+y \leq 4$, $x>1$, $y>0$, $z=x+y-3$ and $z \geq 0$; (b) an ammonium salt; and (c) water; wherein the ammonium salt and the water can be present partially or completely as an aqueous solution of the ammonium salt.

25 Claims, No Drawings

(56) References Cited

OTHER PUBLICATIONS

Hall, D.A., Stevens, R., "Effect of Water Content on the Structure and Mechanical Properties of Magnesia-Phosphate Cement Mortar," Journal of the American Ceramic Society, 1998, vol. 81, No. 6, 1550-1556.

Sarkar, A.K., "Hydration/Dehydration Characteristics of Struvite and Dittmarite Pertaining to Magnesium Ammonium Phosphate Cement Systems," Journal of Materials Science, 1991, vol. 26, 2514-2518.

Hipedinger, N.E., Scian, A.N., Aglietti, E.F., "Magesia-Ammonium Phosphate-Bonded Cordierite Refractory Castables: Phase Evolution on Heating and Mechanical Properties," Cement and Concrete Research, 2004, vol. 34, 157-164.

Kowalczyk, K., Palavit, G., "Chemical Composition of Mortars made from the Magnesia Amidoimidophosphates System," Journal of Materials Science Letters, 1993, vol. 12, 1276-1278.

Sillen, L.G., Martell, A.E., "Stability Constants of Metal-Ion Complexes," The Chemical Society, Burlington House, W.1, 1964, Special Publication No. 17.

Driessens, Boltong, Wenz, Meyer, "Calcium Phosphates as Fillers in Struvite Cements," Key Eng. Mat., vol. 284-286, 2005, pp. 161-164, XP008108642 Switzerland.

\* cited by examiner

PREPARATION FOR MAGNESIUM AMMONIUM PHOSPHATE CEMENTS

BACKGROUND

The invention relates to a preparation for a magnesium ammonium phosphate cement, a process for the production of such a cement, and uses of the so prepared cement.

The healing process of bone defects, the extent of which exceeds a critical size (critical size defects, CSD), requires the use of application site specific transplants or implants to prevent growing of connective tissue into the defect and to restore the lost biofunctionality. Regarding the growing-in behavior and the functional restoration of the autologous transplantation of a body's own bone represents a "gold standard"; however, with large defects it has the disadvantages of lacking availability and the risk of a repeat operation. Therefore, in recent years there were investigated synthetic bone replacement materials. In the clinical application these synthetic bone replacement materials have to fulfill different criteria. In a load-bearing area mechanical properties are mainly the focus and primarily high-tensile metallic materials such as titanium, titanium alloys, stainless steels, and CoCr alloys are used. Importance is attached to a connective tissue free growing in of the material, and a selective resorption and replacement by natural bone in the not or only slightly load-bearing area. Artificial materials with clinical application for such functionally non-load-bearing defects are calcium phosphate ceramics and cements, respectively, bio-glasses, collagens, or lyophilized bone implants. At the application site the materials have to absorb mechanical load only partly and as the mostly porous lead structure should support growing in of new bone.

A main clinical requirement to bone replacement materials is their resorptivity in the physiologic environment regenerating native bone substance. Many of the mentioned materials cannot or only partially fulfill this requirement. For example, sintered ceramics of hydroxyl apatite, or cements of polymethyl methacrylate do not show physiological degradability. Degradable materials with clinical employment are for example tricalcium phosphate ceramics as powders or granules which however, cannot take over a support function in the bone defect. Additionally, in situ formable and hardening mineral cements are known that on the one hand can set to hydroxyl apatite and that only are resorbed over longer periods of time or compositions that after setting consist of calcium hydrogen phosphate·dihydrate (brushite) and can be resorbed medium-term due to their comparatively high solubility in a period of about 3 to 6 months. Reservations regarding a wide-ranging clinical application of such brushite cements result from the comparatively low mechanical strength, as well as the strongly acidic pH value of the materials during and after the setting process that can result in the release of acidic phosphate ions into the surrounding tissue.

SUMMARY

A further and new alternative represents magnesium ammonium phosphate cements which set within a short period of time (<5 to 10 min.) to magnesium ammonium phosphate·hexahydrate $((NH_4)MgPO_4 \cdot 6(H_2O)$, struvite). Struvite represents a biological calcification and is found, for example, after bacterial infection in nephroliths. Cement formulations forming struvite as setting product showed very good mechanical properties with a compressive strength >50 MPa and a setting time of 3 to 10 min. Thereby, the setting reaction of the cements takes place in the neutral pH value range because both the powder components ($MgHPO_4$, $Mg_3(PO_4)_2$) and the liquid cement phase (($NH_4)_2HPO_4$) are almost neutral. From the solubility product of struvite ($LP=5.21 \times 10^{-15}$ (pK(sp)=14.28) to $LP=2.12 \times 10^{-13}$ (pK(sp)=12.67) in the pH range of 7.01–9.62) a substantially better resorptivity in the region of the bone transplant can be expected as opposed to materials based on hydroxyl apatite (pK=59) or tricalcium phosphate (pK=29).

The studies about struvite cements known from the literature each used multiple-component powder mixtures of secondary ($MgHPO_4$) and tertiary ($Mg_3(PO_4)_2$) magnesium phosphates in association with calcium orthophosphates (α-TCP, β-TCP, HA) as fillers. For example, from DE 100 32 220 A1 cement formulations with a Mg/P molar ratio of 0<Mg/P<0.50, and a Ca/P molar ratio of 0<Ca/P<1.50 are known.

Here, the use of multiple-component powder mixtures can result in problems in view of the homogenous miscibility with different particle sizes or of separation processes in the case of storage and transport of the materials.

An object of the invention is to eliminate the disadvantages according to the state of the art. In particular, a preparation for the production of magnesium ammonium phosphate cements is provided that on the one hand have good mechanical properties, and high resorptivity, and on the other hand use a one-component calcium and magnesium source so that a simplified preparation with a defined setting time is obtained.

BRIEF DESCRIPTION

In accordance to the invention there is provided a preparation for a magnesium ammonium phosphate cement comprising (a) a magnesium calcium phosphate of the formula $Mg_xCa_y(PO_4)_2O_z$, wherein $x+y \leq 4$, $x>1$, $y>0$, $z=x+y-3$ and $z \geq 0$;
(b) an ammonium salt; and
(c) water;

wherein the ammonium salt and the water may be present partially or completely as aqueous solution of the ammonium salt.

When $x+y<3$ then z is strictly 0. When $x+y \geq 3$ then z is in the range of 0 to 1, wherein preferably z=0. In a particularly preferred embodiment $x+y=3$ and $z=0$.

The magnesium calcium phosphate has a Mg/P molar ratio in the range of 0.5<Mg/P<2 and a Ca/P molar ratio in the range of 0<Ca/P<1.

Preferred is $x \geq 2$. Further preferred are a magnesium calcium phosphate with $2.0<x \leq 2.75$ or mixtures of magnesium calcium phosphates with $2.0<x \leq 2.75$.

The invention is based on the finding that a successive replacement of magnesium ions by calcium ions in the synthesis of compounds of the type $Mg_xCa_y(PO_4)_2O_z$ setting with aqueous ammonium phosphate solution to struvite permits a defined adjustment of the setting time.

The hardened magnesium ammonium phosphate cements prepared by means of the preparation in accordance to the invention have a high strength, in particular a compressive strength of more than 30 MPa after 24 h of hardening at 37° C. For the production of the magnesium ammonium phosphate cement the components of the preparation are mixed until a homogenous mixture, the cement paste, is obtained. During the setting process the cement paste has a neutral or almost neutral pH value that makes physiological applications of the preparation easier. The hardened magnesium ammonium phosphate cement can be chemically resorbed by electrolytes, which is attributable to the comparatively high solubility of the setting product struvite.

Preferably, the magnesium calcium phosphate is prepared from a mixture consisting of the compounds calcium hydrogen phosphate ($CaHPO_4$), calcium carbonate ($CaCO_3$), magnesium hydrogen phosphate trihydrate ($MgHPO_4 \cdot 3H_2O$), and magnesium hydroxide ($Mg(OH)_2$). Alternatively, other magnesium or calcium compounds may be employed, for example CaO, $Ca(OH)_2$, $CaHPO_4 \cdot 2H_2O$, $Ca(NO_3)_2$, MgO, $MgCO_3$, $Mg(NO_3)_2$, etc. For that, powdered compounds are mixed in a given stoichiometric ratio. Here, the mixing ratio is selected such that the conditions for x and y and z in the formula $Mg_xCa_y(PO_4)_2O_z$ are fulfilled. After homogenously mixing the compounds the so obtained mixture is sintered to obtain the product with the formula $Mg_xCa_y(PO_4)_2O_z$. Preferably, sintering is performed at temperatures of more than 800° C. and for a period of time of 1-100 h. By means of sintering, the magnesium calcium phosphate is obtained as a solid one-component compound. Here, the term "one-component" means a homogenous composition also in the microscopic scale; however in this case, several, not distinctly identifiable crystalline calcium and magnesium phosphate phases may be present in the single grains. Subsequently, the sinter cake is comminuted and the comminuting product is grinded to a given initial particle size. After grinding, the particle size should be 0.1 µm to approximately 100 µm, wherein it might be of advantage to specifically combine fractions with different particle sizes. It is particularly preferred that the mean particle size of the powdery magnesium calcium phosphate is in the range of 0.5 to 10 µm. By means of grinding, the magnesium calcium phosphate is obtained in the form of a powder. Here, the grinding not only results in the comminution of the magnesium calcium phosphate particles but also in a partial amorphization (mechanical activation) resulting in an increased solubility and reactivity of the magnesium calcium phosphate particle obtained by grinding.

Preferred magnesium calcium phosphates are e.g., $Mg_{2.25}Ca_{0.75}(PO_4)_2$, $Mg_{2.5}Ca_{0.5}(PO_4)_2$, and $Mg_{2.75}Ca_{0.25}(PO_4)_2$. Also mixtures of these compounds can be employed. However, because the exemplarily given compositions are not defined compounds in the sense of crystallography also deviating compositions of Mg, Ca, and ($PO_4$) can be chosen. Particularly preferred are compositions in accordance to the following formula $Mg_{2.0-2.9}Ca_{0.1-1.0}(PO_4)_2$.

Preferably, the preparation comprises the ammonium salt in the form of an aqueous solution. For the production of the magnesium ammonium phosphate cement the aqueous ammonium salt solution is then mixed with the solid powdered magnesium calcium phosphate until a homogenous mixture is obtained. Hereinafter, the homogenous mixture is also referred to as cement paste. The ratio of solid powdered magnesium calcium phosphate to the aqueous ammonium salt solution (powder/liquid ratio) is preferably 1.0 to 5.0 g/ml, more preferred 2.5 to 5.0 g/ml, particularly preferred 2.5 to 3.5 g/ml.

Alternatively, the ammonium salt however may also be mixed with the powdered magnesium calcium phosphate partially or completely as a solid powdered ammonium salt. By doing so, a high powder/liquid ratio can be obtained in which case a solution of just the ammonium salt would not provide a sufficient concentration of ammonium ions for a complete setting due to its limited solubility. The powdery solid mixture is then mixed with water to obtain the cement paste. The ratio of the solid powdery mixture of magnesium calcium phosphate and ammonium salt to water (powder/liquid ratio) is preferably 1.0 to 5.0 g/ml, more preferred 2.5 to 5.0 g/ml, particularly preferred 2.5 to 3.5 g/ml.

Preferably, the ammonium salt is an ammonium phosphate, particularly preferred a diammonium hydrogen phosphate. Preferably, the diammonium hydrogen phosphate is present as a 3.5M aqueous solution. Also particularly preferred are mixtures of diammonium hydrogen phosphate and ammonium dihydrogen phosphate at comparable total concentration. Also, alternative ammonium salts can be used, for example in particular the monoammonium salts and/or the diammonium salts of citric acid, tartaric acid, sulfuric acid, and acetic acid, or their mixtures.

The production of the magnesium ammonium phosphate cement using the preparation according to the invention preferably comprises the following steps:

(a) mixing the magnesium calcium phosphate with the ammonium salt and the water and/or with an aqueous solution of the ammonium salt until a homogenous mixture (cement paste) is obtained;

(b) application or introduction of the homogenous mixture to or in a target object; and (c) causing the homogenous mixture to harden obtaining the set magnesium ammonium phosphate cement.

Preferably, in step (a) powdered magnesium calcium phosphate is homogenously mixed with an aqueous solution of the ammonium salt. Preferably, the ammonium salt is diammonium hydrogen phosphate or a mixture of diammonium hydrogen phosphate and ammonium dihydrogen phosphate, or ammonium dihydrogen phosphate.

The setting time of the cement paste can be adjusted by various mechanisms. Reduction of the setting time is achieved either by extending the grinding period and/or by increasing the concentration of the ammonium salt in the preparation, for example by increasing its concentration in the aqueous solution. Alternatively, (in particular when the solubility limit is reached) a part (or all) of the ammonium salt can be incorporated into the powder component.

The viscosity of the cement paste may be decreased by reducing the powder/liquid ratio so that the paste can also be injected through thin cannulas, whereby the mechanical properties are not deteriorated, as is known with calcium phosphate cements.

The preparation according to the invention is used for the production of a magnesium ammonium phosphate cement. The magnesium ammonium phosphate cement can be employed for medical purposes, for example as bone cement, bone replacement, and/or as bone filler or bone adhesive. In addition, the magnesium ammonium phosphate cement can be used for the production of preformed implants. Such implants may for example be prepared by 3D powder printing.

Basically, the combination of mineral bone cements with various excipients is known from the literature, in particular such excipients that can affect the injectivity, cohesion, paste consistency, porosity, resorptivity, adhesion to the bone, stability in storage, compatibility with active ingredients and their release in the desired manner. All these excipients can also be combined with the cement composition described herein.

The same applies for pharmacologically active ingredients. The magnesium ammonium phosphate cement according to the invention is particularly suitable as a supporting material for active ingredients since it is composed of largely pH neutral components and also the setting product reacts neutrally. Particularly preferred is the combination of the cement with active ingredients which promote the bone formation, suppress inflammatory reactions in the environment of the implanted material, suppress the bone resorption, and/or are suitable for the control of microbial infections or contaminations.

The preparation according to the invention or the cement obtained by means of the preparation according to the invention can be combined with pharmaceutically active ingredients. Exemplary pharmaceutically active ingredients are antibiotics, bone growth factors, cytostatic agents, and anti-inflammatory agents, this list being not exhaustive.

When the pharmaceutically active ingredients are water-soluble they are preferably added to the liquid phase of the preparation. Alternatively, the pharmaceutically active ingredients can be added to the obtained cement. In this case, the pharmaceutically active ingredient may for example be added to the powdery cement directly or encapsulated in a degradable polymer. By the encapsulation in a degradable polymer the releasing kinetics of the pharmaceutically active ingredient can be controlled advantageously.

Moreover, the preparation according to the invention or the cement obtained by means of the preparation according to the invention can be combined with excipients. Examples of excipients are viscosity affecting additives for enhancing the injectivity as well as the cohesion of the cement paste, for example water-soluble polymers or multiple charged anions for the electrostatic charging of the particles of the cement; particulate or fibrous ceramic or polymeric substances for the reinforcement of the cement matrix and for the formation of pores after leaching, this list being not exhaustive.

The magnesium ammonium phosphate cement obtained from the preparation according to the invention has a high compressive strength and a good resorptivity in the human or animal body.

The invention is explained in more detail below with reference to examples.

EXAMPLES

The production of magnesium calcium phosphates according to the invention was carried out by sintering powder mixtures with the stoichiometry given in table 1 at a temperature of 1,100° C. and a sinter period of 5 h. Then, the sinter cake was comminuted manually to a particle size <355 μm and grinded in a planetary ball mill for a period of time of 10 min. to 24 h. The mean size of the obtained magnesium calcium phosphate particles is stated in table 2.

TABLE 1

Composition of the powder mixture for the production of the compounds of the formula $Mg_xCa_y(PO_4)_2O_z$ (z = 0)

| $Mg_xCa_y(PO_4)_2$ | $CaHPO_4$ [mol] | $CaCO_3$ [mol] | $MgHPO_4·3H_2O$ [mol] | $Mg(OH)_2$ [mol] |
|---|---|---|---|---|
| $Mg_{1.5}Ca_{1.5}(PO_4)_2$ | 1 | 0.5 | 1 | 0.5 |
| $Mg_{2.25}Ca_{0.75}(PO_4)_2$ | 0.5 | 0.25 | 1.5 | 0.75 |
| $Mg_{2.5}Ca_{0.5}(PO_4)_2$ | 0.33 | 0.17 | 1.67 | 0.83 |
| $Mg_{2.75}Ca_{0.25}(PO_4)_2$ | 0.167 | 0.083 | 1.83 | 0.92 |
| *$Mg_3(PO_4)_2$ | — | — | 2 | 1 |

*Comparative example

TABLE 2

Mean Particle Size in μm of $Mg_xCa_y(PO_4)_2O_z$ (z = 0)

| Grinding period [h] | $Mg_{1.5}Ca_{1.5}(PO_4)_2$ | $Mg_{2.25}Ca_{0.75}(PO_4)_2$ | *$Mg_3(PO_4)_2$ |
|---|---|---|---|
| not grinded | 41.1 ± 14.2 | 23.8 | 47.8 ± 1.3 |
| 1 h | 16.2 ± 1.6 | 7.7 ± 0.2 | 10.5 ± 2.6 |
| 4 h | 7.3 ± 3.0 | 6.09 ± 0.1 | 7.5 ± 0.4 |
| 24 h | 5.1 ± 1.1 | 0.6 ± 0.1 | 2.7 ± 1.7 |

*Comparative example

The thus obtained powders were mixed with a 3.5M aqueous $(NH_4)_2HPO_4$ solution as the liquid phase into a cement paste. Here, the powder/liquid ratio (P/L) was varied in the range of 1.0 to 3.5 g/ml. The setting times of the cement paste were determined by the Gilmore needle test at 37° C. and >90% relative humidity (tables 3 and 4).

TABLE 3

Setting times of a cement paste of $Mg_xCa_y(PO_4)_2O_z$ (z = 0) and a 3.5M $(NH_4)_2HPO_4$ solution as the liquid phase (P/L = 3.0 g/ml), measured by the Gilmore needle test

| Grinding period [h] | $Mg_{1.5}Ca_{1.5}(PO_4)_2$ | $Mg_{2.25}Ca_{0.75}(PO_4)_2$ | *$Mg_3(PO_4)_2$ |
|---|---|---|---|
| 1 h | 32 min. | 14 min. | 4 min. |

*Comparative example

TABLE 4

Setting times of a cement composition of $Mg_xCa_y(PO_4)_2O_z$ (z = 0) with a 3.5M $(NH_4)_2HPO_4$ solution as the liquid phase in dependence on the powder/liquid ratio (P/L), measured by the Gilmore needle test

| | $Mg_{2.5}Ca_{0.5}(PO_4)_2$ | | $Mg_{2.75}Ca_{0.25}(PO_4)_2$ | |
|---|---|---|---|---|
| P/L [g/ml] | 1 h Grinding period | 4 h Grinding period | 1 h Grinding period | 4 h Grinding period |
| 3.0 | 8 min. | 4 min. | 8 min. | 3 min. 30 sec. |
| 2.5 | 13 min. | 8 min. | 12 min. | 6 min. 30 sec. |
| 2.0 | 18 min. | 13 min. | 19 min. | 14 min. |
| 1.5 | 22 min. | 19 min. | 23 min. | 18 min. |

For the determination of the compressive strength of the magnesium ammonium phosphate cements prepared by means of the preparation according to the invention the cement paste was filled into silicone moulds and hardened for 24 h at 37° C. Cartesian specimens of the dimension 12×6×6 mm resulted, which were loaded with a universal test machine along the longitudinal axis, until breaking. The compressive strength was calculated from the breaking strength and the cross-sectional area (tables 5 and 6).

TABLE 5

Compressive strength of magnesium ammonium phosphate cements prepared from $Mg_xCa_y(PO_4)_2O_z$ (z = 0) and a 3.5M $(NH_4)_2HPO_4$ solution as the liquid phase (P/L = 3.0 g/ml) after 24 h of hardening at 37° C. and 100% relative humidity

| Grinding period[1] [h] | $Mg_{1.5}Ca_{1.5}(PO_4)_2$ | $Mg_{2.25}Ca_{0.75}(PO_4)$ | $Mg_{2.5}Ca_{0.5}(PO_4)_2$ | $Mg_{2.75}Ca_{0.25}(PO_4)_2$ | *$Mg_3(PO_4)_2$ |
|---|---|---|---|---|---|
| 1 h | 16.0 ± 2.8 | 42.3 ± 9.6 | 21.8 ± 4.0 | 25.7 ± 4.3 | 61.2 ± 6.0 |
| 4 h | 21.2 ± 3.5 | 72.7 ± 8.8 | 77.1 ± 6.4 | 53.8 ± 6.3 | 58.6 ± 9.5 |
| 24 h | — | — | — | — | 42.3 ± 9.6 |

[1]grinding period of the stated sintered magnesium calcium phosphate
*Comparative example
— not determined

TABLE 6

Compressive strength of magnesium ammonium phosphate cements prepared from $Mg_xCa_y(PO_4)_2O_z$ (z = 0) powdered by use of different grinding periods and a 3.5M $(NH_4)_2HPO_4$ solution as the liquid phase with different powder/liquid ratios (P/L) after 24 h of hardening at 37° C.

| | $Mg_{2.5}Ca_{0.5}(PO_4)_2$ | | $Mg_{2.75}Ca_{0.25}(PO_4)_2$ | |
|---|---|---|---|---|
| P/L [g/ml] | 1 h Grinding period | 4 h Grinding period | 1 h Grinding period | 4 h Grinding period |
| 3.0 | 21.8 ± 4.01 | 77.1 ± 6.4 | 25.7 ± 4.3 | 53.8 ± 6.3 |
| 2.5 | 17.4 ± 4.1 | 55.6 ± 7.4 | 20.3 ± 4.3 | 52.7 ± 6.6 |
| 2.0 | 16.7 ± 6.8 | 15.2 ± 4.9 | 15.3 ± 4.9 | 12.2 ± 5.4 |
| 1.5 | 12.4 ± 4.3 | 15.0 ± 4.5 | 13.7 ± 4.5 | 15.0 ± 4.7 |

The embodiments have been described, hereinabove. It will be apparent to those skilled in the art that the above methods and apparatuses may incorporate changes and modifications without departing from the general scope of this invention. It is intended to include all such modifications and alterations insofar as they come within the scope of the appended claims or the equivalents thereof. Although the description above contains much specificity, this should not be construed as limiting the scope of the invention, but as merely providing illustrations of some of the embodiments of this invention. Various other embodiments and ramifications are possible within its scope.

Furthermore, notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Having thus described the invention, it is now claimed:

1. A composition for a magnesium ammonium phosphate cement comprising:
   (a) a magnesium calcium phosphate of the formula $Mg_xCa_y(PO_4)_2O_z$, wherein x+y≦4, x>1, y>0, z=x+y−3 and z≧0;
   (b) an ammonium salt; and
   (c) water.

2. The composition according to claim 1 wherein the magnesium calcium phosphate has a Mg/P molar ratio in the range of 0.5<Mg/P<2.0 and a Ca/P molar ratio in the range of 0<Ca/P<1.

3. The composition according to claim 1 wherein x≧2.

4. The composition according to claim 1 wherein the magnesium calcium phosphate is a magnesium calcium phosphate of the formula $Mg_{2.0-2.9}Ca_{0.1-1.0}(PO_4)_2$ or a mixture of magnesium calcium phosphates of this formula.

5. The composition according to claim 3 wherein the magnesium calcium phosphate is a magnesium calcium phosphate with 2.0<x≦2.75 or a mixture of magnesium calcium phosphates with 2.0<x≦2.75.

6. The composition according to claim 5 wherein the magnesium calcium phosphate is selected from the group consisting of $Mg_{2.25}Ca_{0.75}(PO_4)_2$, $Mg_{2.5}Ca_{0.5}(PO_4)_2$, $Mg_{2.75}Ca_{0.25}(PO_4)_2$, and mixtures thereof.

7. The composition according to claim 1 wherein the magnesium calcium phosphate is a sintered magnesium calcium phosphate.

8. The composition according to claim 1 wherein the magnesium calcium phosphate is a powder and has a mean particle size in the range of 0.5 to 10 µm.

9. The composition according to claim 1 wherein the ammonium salt is selected from the group consisting of monoammonium salts of phosphoric acid, monoammonium salts of citric acid, monoammonium salts of tartaric acid, monoammonium salts of sulfuric acid, monoammonium salts of acetic acid, diammonium salts of phosphoric acid, diammonium salts of citric acid, diammonium salts of tartaric acid, diammonium salts of sulfuric acid, diammonium salts of acetic acid, and mixtures thereof.

10. The composition according to claim 1 wherein the ammonium salt is selected from the group consisting of diammonium hydrogen phosphate, ammonium dihydrogen phosphate, and a mixture of diammonium hydrogen phosphate and ammonium dihydrogen phosphate.

11. The composition according to claim 10 wherein the ammonium salt is present as a 3.5M aqueous solution.

12. The composition according to claim 5 wherein the ammonium salt is admixed to the magnesium calcium phosphate partially or completely in solid form as a powder.

13. The composition according to claim 1 wherein the ratio of magnesium calcium phosphate to water or to the aqueous solution is 1.0 to 5.0 g/ml.

14. The composition according to claim 1 wherein the composition further comprises pharmaceutically active ingredients.

15. The composition according to claim 1 wherein the composition further comprises viscosity affecting excipients.

16. The composition according to claim 1 wherein the composition further comprises pore forming excipients.

17. A process for the production of a magnesium ammonium phosphate cement using a composition comprising:
   (a) mixing magnesium calcium phosphate of the formula $Mg_xCa_y(PO_4)_2O_z$, wherein x+y≦4, x>1, y>0, z=x+y−3 and z≧0 with ammonium salt and water or with an aqueous solution of the ammonium salt until a homogenous mixture is obtained;
   (b) applying the homogenous mixture to a target object; and (c) causing the homogenous mixture to harden, thereby obtaining set magnesium ammonium phosphate cement.

18. The process according to claim 17 wherein step (a) comprises mixing the magnesium calcium phosphate of the formula $Mg_xCa_y(PO_4)_2O_z$, wherein $x+y \leqq 4$, $x>1$, $y>0$, $z=x+y-3$ and $z \geqq 0$ with the aqueous solution of the ammonium salt.

19. The process according to claim 17, wherein the magnesium ammonium phosphate cement is used for at least one of the group comprising bone replacement, bone filler, and bone adhesive.

20. The process according to claim 17, wherein the magnesium ammonium phosphate cement is used for a preformed implant.

21. The process according to claim 17 wherein the composition or the magnesium ammonium phosphate cement acts as a support for pharmaceutically active ingredients.

22. The composition according to claim 1 wherein the composition further comprises at least one selected from the group consisting of viscosity affecting and pore forming excipients.

23. A composition for a magnesium ammonium phosphate cement comprising:
(a) a magnesium calcium phosphate of the formula $Mg_xCa_y(PO_4)_2O_z$, wherein $x+y \leqq 4$, $x>1$, $y>0$, $z=x+y-3$ and $z \geqq 0$, wherein the magnesium calcium phosphate is selected from the group consisting of sintered magnesium calcium phosphate, powdered magnesium calcium phosphate having a mean particle size in the range of 0.5 to 10 μm, $Mg_{2.25}Ca_{0.75}(PO_4)_2$, $Mg_{2.5}Ca_{0.5}(PO_4)_2$, and $Mg_{2.75}Ca_{0.25}(PO_4)_2$;

(b) an ammonium salt, wherein the ammonium salt is selected from the group consisting of monoammonium salts of phosphoric acid, monoammonium salts of citric acid, monoammonium salts of tartaric acid, monoammonium salts of sulfuric acid, monoammonium salts of acetic acid, diammonium salts of phosphoric acid, diammonium salts of citric acid, diammonium salts of tartaric acid, diammonium salts of sulfuric acid, diammonium salts of acetic acid, and mixtures thereof, diammonium hydrogen phosphate, ammonium dihydrogen phosphate, and a mixture of diammonium hydrogen phosphate and ammonium dihydrogen phosphate;

(c) water; and, (d) at least one of the group comprising pharmaceutically active ingredients, viscosity affecting excipients, pore forming excipients, injectivity affecting excipients, cohesion affecting excipients, paste consistency affecting excipients, porosity affecting excipients, resorptivity affecting excipients, adhesion to the bone affecting excipients, stability in storage affecting excipients, compatibility with active ingredients affecting excipients, and release affecting excipients.

24. The composition according to claim 1 wherein the ammonium salt and the water is present as an aqueous solution of the ammonium salt.

25. The composition according to claim 23 wherein the ammonium salt and the water is present as an aqueous solution of the ammonium salt.

* * * * *